US006537263B1

(12) United States Patent
Aneas

(10) Patent No.: US 6,537,263 B1
(45) Date of Patent: Mar. 25, 2003

(54) DEVICE FOR CONNECTING A RECEPTACLE AND A CONTAINER AND READY-FOR-USE SET COMPRISING SAME

(75) Inventor: Antoine Aneas, Menetrol (FR)

(73) Assignee: Biodome, Issoire (FR)

( * ) Notice: Subject to any disclaimer, the term of this patent is extended or adjusted under 35 U.S.C. 154(b) by 0 days.

(21) Appl. No.: 09/787,578

(22) PCT Filed: Sep. 23, 1999

(86) PCT No.: PCT/FR99/02268

§ 371 (c)(1),
(2), (4) Date: Mar. 19, 2001

(87) PCT Pub. No.: WO00/16730

PCT Pub. Date: Mar. 30, 2000

(30) Foreign Application Priority Data

Sep. 24, 1998 (FR) ............................................ 98 12120

(51) Int. Cl.$^{7}$ ................................................ A61B 19/00

(52) U.S. Cl. ....................... 604/412; 604/415; 604/416; 604/413; 604/411; 604/403

(58) Field of Search ................................ 604/412, 413, 604/414, 415, 416, 411, 403

(56) References Cited

U.S. PATENT DOCUMENTS

| | | | | | |
|---|---|---|---|---|---|
| 2,847,996 | A | | 8/1958 | Cohen et al. | |
| 3,902,491 | A | | 9/1975 | Lajus | |
| 3,976,073 | A | * | 8/1976 | Quick et al. | 128/272 |
| 4,195,632 | A | | 4/1980 | Parker et al. | |
| 4,296,786 | A | | 10/1981 | Brignola | |
| 4,507,113 | A | | 3/1985 | Dunlap | |
| 4,552,277 | A | | 11/1985 | Richardson et al. | |
| 4,576,211 | A | | 3/1986 | Valentini et al. | |
| 4,589,879 | A | | 5/1986 | Pearson | |
| 4,607,671 | A | * | 8/1986 | Aalto et al. | 141/329 |
| 4,639,250 | A | | 1/1987 | Rycroft | |
| 4,675,020 | A | * | 6/1987 | McPhee | 604/411 |
| 4,713,060 | A | | 12/1987 | Riuli | |
| 4,759,756 | A | * | 7/1988 | Forman et al. | 604/413 |

(List continued on next page.)

FOREIGN PATENT DOCUMENTS

| | | |
|---|---|---|
| DE | 41 22 476 A1 | 1/1993 |
| DE | 295 16 650 U1 | 2/1996 |
| EP | 0 458 543 A1 | 11/1991 |
| EP | 0 538 891 A1 | 4/1993 |
| EP | 0 737 485 A1 | 10/1996 |
| EP | 0 728 457 A2 | 11/1996 |
| EP | 0 728 457 A3 | 11/1996 |
| EP | 0 829 250 A2 | 3/1998 |
| EP | 0 829 250 A3 | 3/1998 |
| EP | 0 728 457 B1 | 1/1999 |
| FR | 1423549 | 2/1965 |
| FR | 2753624 A1 | 3/1998 |
| WO | WO 90/03536 A1 | 4/1990 |
| WO | WO90/03536 | 4/1990 |
| WO | WO 96/00053 A1 | 1/1996 |
| WO | WO 97/10156 A1 | 3/1997 |
| WO | WO97/10156 | 3/1997 |
| WO | WO 98/13006 A1 | 4/1998 |
| WO | WO 99/27886 A1 | 6/1999 |
| WO | WO 99/53886 A1 | 10/1999 |

*Primary Examiner*—Ira S. Lazarus
*Assistant Examiner*—Tu Cam Nguyen
(74) *Attorney, Agent, or Firm*—Wallenstein & Wagner, Ltd.

(57) ABSTRACT

The invention concerns a connecting device (1) comprising a base (5) mounted on the receptacle (2) and extended by a flange (9) forming an inner bore (A) and a piston (10) capable of sliding in said inner bore (A) between a released position relative to a plug (4) and a transfer position wherein a hollow needle (11) borne by the piston (10) passes through the plug (4). A scaling lip (22) is arranged on an internal surface (8*d*) of the bore (A) opposite the piston (10) or a surface of the piston, said lip (22) being shaped to be urged to press sealingly against the piston (10*d*) or against an internal surface of the bore, in the transfer position.

16 Claims, 6 Drawing Sheets

U.S. PATENT DOCUMENTS

| | | | | | |
|---|---|---|---|---|---|
| 4,883,483 | A | | 11/1989 | Lindmayer | |
| 4,898,209 | A | * | 2/1990 | Zhed | 604/414 |
| 5,060,704 | A | * | 10/1991 | Rohrbough | 141/132 |
| 5,152,965 | A | | 10/1992 | Fisk et al. | |
| 5,169,388 | A | * | 12/1992 | McPhee | 604/90 |
| 5,186,323 | A | | 2/1993 | Pfleger | |
| 5,224,515 | A | | 7/1993 | Foster et al. | |
| 5,232,029 | A | | 8/1993 | Knox et al. | |
| 5,247,972 | A | | 9/1993 | Tetrault | |
| 5,279,576 | A | | 1/1994 | Loo et al. | |
| 5,279,583 | A | | 1/1994 | Shober, Jr. et al. | |
| 5,308,347 | A | | 5/1994 | Sunago et al. | |
| 5,336,180 | A | * | 8/1994 | Kriesel et al. | 604/82 |
| 5,342,346 | A | | 8/1994 | Honda et al. | |
| 5,342,347 | A | | 8/1994 | Kikuchi et al. | |
| 5,350,372 | A | | 9/1994 | Ikeda et al. | |
| 5,352,191 | A | | 10/1994 | Sunago et al. | |
| 5,364,386 | A | | 11/1994 | Fukuoka et al. | |
| 5,374,264 | A | | 12/1994 | Wadsworth, Jr. | |
| 5,397,303 | A | | 3/1995 | Sancoff et al. | |
| 5,423,753 | A | | 6/1995 | Fowles et al. | |
| 5,423,791 | A | | 6/1995 | Bartlett | |
| 5,429,256 | A | | 7/1995 | Kestenbaum | |
| 5,429,614 | A | | 7/1995 | Fowles et al. | |
| 5,478,337 | A | | 12/1995 | Okamoto et al. | |
| 5,526,853 | A | | 6/1996 | McPhee et al. | |
| 5,636,660 | A | | 6/1997 | Pfleiderer et al. | |
| 5,653,686 | A | * | 8/1997 | Coulter et al. | 604/56 |
| 5,701,910 | A | * | 12/1997 | Powles et al. | 128/764 |
| 5,772,652 | A | * | 6/1998 | Zielinski | 604/411 |
| 5,807,323 | A | * | 9/1998 | Kriesel et al. | 604/89 |
| 5,873,872 | A | * | 2/1999 | Thibault et al. | 604/414 |
| 5,879,345 | A | * | 3/1999 | Aneas | 604/411 |
| 5,925,029 | A | * | 7/1999 | Jansen et al. | 604/411 |
| 6,063,068 | A | * | 5/2000 | Fowles et al. | 604/414 |
| 6,070,623 | A | | 6/2000 | Aneas | |
| 6,022,339 | A | | 8/2000 | Fowles et al. | |
| 6,213,994 | B1 | * | 4/2001 | Jansen et al. | 604/415 |
| 6,299,608 | B1 | * | 10/2001 | Solomon et al. | 604/411 |

* cited by examiner 1
9
10a
V'
5
8c
3b
6
3
24
-A-
B
8a
9a
20
Y'
3a
X
X'
10b
Y
10
V
22
4b
10d
11
4a
4
15
10c
J
8d
8
8b
13
6
2

DEVICE FOR CONNECTING A RECEPTACLE AND A CONTAINER AND READY-FOR-USE SET COMPRISING SAME

The invention relates to a device for connecting a closed receptacle and a container. The invention also relates to a ready-for-use set comprising, inter alia, a closed receptacle and a connection device of the afore-mentioned type.

In the domain of drug-packaging, it is known to store a component of a medicinal preparation, such as for example its active ingredient, in a recipient closed by a stopper of relatively non-rigid material, for example of elastomer. A liquid may be introduced into this recipient after perforation of the stopper in order to dissolve the component contained in the recipient or place it in suspension, with a view to obtaining a medicinal preparation in liquid form ready to be administered to the patient.

Document WO-A-97110156 discloses a connection device of the afore-mentioned type which comprises a base adapted to cover the neck of the recipient and extends in a flange forming an inner bore while a plunger is adapted to slide in this bore, between a position disengaged with respect to the stopper and a transfer position in which a hollow needle borne by the plunger traverses this stopper. The displacement of the plunger from its disengaged position towards its transfer position is effected manually by an operator. During this manipulation, it happens that the operator exerts on the flange for guiding the plunger or on the latter in the course of displacement, a transverse effort which may result in a perforation of the stopper in an inclined direction with respect to a central axis of symmetry of the stopper. The functional clearance between the plunger and the inner bore of the base cannot be reduced too significantly in order to allow a better axial guiding of the plunger, as the effort resisting the displacement of the plunger would in that case be too great. The risk of an inclined or "slantwise" perforation of the stopper is therefore non-negligible, in particular when the user has to prepare a medicament urgently.

The consequence of a slantwise perforation of the stopper is that the apparent section of the orifice, created in the stopper by the passage of the hollow needle, is greater than the outer diameter of this needle, to such an extent that leakages may be produced through the stopper, around the hollow needle. In particular, when the recipient and the container with which it is associated are placed in a position of flow by gravity of the reconstituted medicament from the recipient towards the container, i.e. when the recipient is placed above the container, it is possible that the medicinal preparation flows from the recipient towards the plunger and flows over the user's hands, which may be dangerous for certain medicaments or unpleasant for less aggressive medicaments.

It is a more particular object of the invention to overcome these drawbacks by proposing an improvement in the known systems which allow their tightness to be guaranteed, including in the case of slantwise perforation of the stopper that they comprise.

The device of the invention is characterized in that it comprises a sealing lip arranged on an internal surface of the bore opposite the plunger or on a surface of the plunger, this lip being shaped to be in tight abutment against the plunger or against an internal surface of the bore, in the transfer position of the plunger.

Thanks to the invention, there is created a volume of containment around the hollow needle, between the plunger and the internal surface of the bore, this volume of containment making it possible to retain liquid possibly leaking outside the recipient through the orifice formed in the stopper by the hollow needle.

According to a first, advantageous variant embodiment of the invention, the base comprises a wall bearing against an outer part of the stopper, the lip being shaped on a face of this wall oriented towards the plunger. According to a second, advantageous variant embodiment, the lip is shaped on a front face of the plunger oriented towards the stopper. According to another advantageous variant embodiment, the lip is shaped on an inner radial surface of the flange or on an outer radial surface of the plunger.

In any case, the lip may be provided to present, in transverse section, an asymmetrical profile inducing a privileged direction of deformation. This aspect of the invention guarantees an adequate positioning of the lip when the plunger is in transfer position, this adequate positioning guaranteeing the desired seal.

According to another advantageous aspect of the invention, the flange bears, on its inner radial face, a circular ring adapted to cooperate with a corresponding shoulder of the outer radial surface of the plunger in order to lock this plunger in the transfer position. Locking of the plunger has the effect of precisely fixing the position of the plunger and consequently the crushing or deformation of the sealing lip, which ensures a tight contact between the lip and the surface with which it must cooperate. The ring may be provided to present an asymmetrical tranverse section, the face of the ring oriented towards the opening of the bore being less inclined with respect to the inner radial surface of the flange than the face of the ring oriented towards the stopper. This arrangement allows the ring not, or hardly, to hinder the movement of slide of the plunger in the direction of the stopper, from its disengaged position towards its transfer position, while it may efficiently oppose a movement of the plunger in the opposite direction. The ring is advantageously adapted to separate an annular volume defined in the bore around the front part of the plunger in transfer position, in tight manner from the ambient atmosphere. In that case, the ring performs a function of seal which is added to that of the lip mentioned hereinbefore.

The invention also relates to a ready-for-use assembly comprising a closed recipient containing a product, this recipient comprising a neck whose opening is obturated by a stopper made of relatively non-rigid material, and a connection device as described hereinabove, mounted on the recipient. Such an assembly makes it possible to conserve a component of a medicament, such as its active ingredient, sterile, and to prepare it when required by mixture with a liquid, without risk of dangerous or unpleasant leakage.

The invention will be more readily understood and other advantages thereof will appear more clearly on reading the following description of three embodiments of a connection device in accordance with its principle, given solely by way of example and made with reference to the accompanying drawings, in which.

Figure 1:
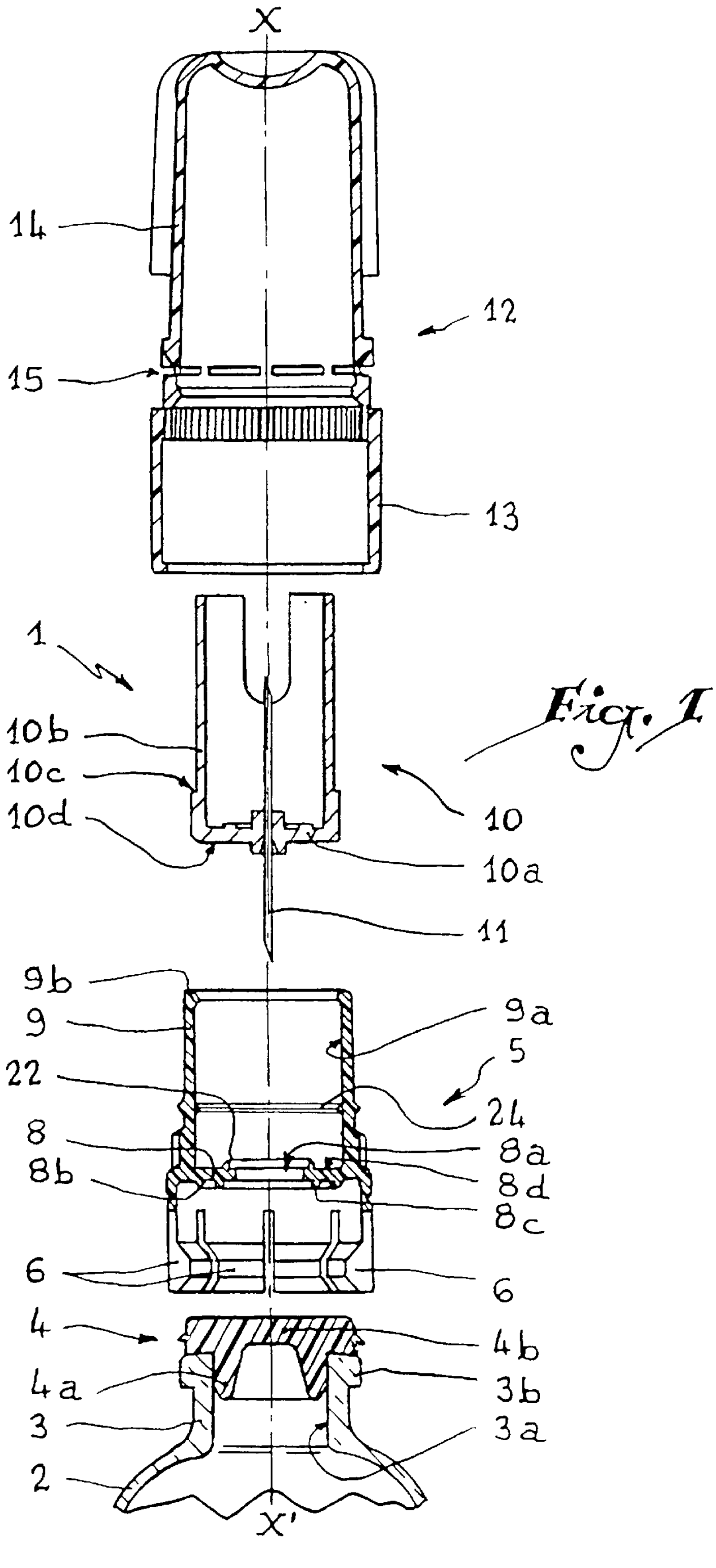
FIG. 1 is a longitudinal section, in exploded view, of a connection device according to the invention and of a recipient on which it is provided to be mounted.

The device 1 according to the invention has a dual function. On the one hand, it renders tamperproof a recipient 2, for example a glass flask, containing a product (not shown) and previously closed or stoppered. On the other hand, it ensures or establishes a tight connection between the interior of the recipient 2 and the interior of another container 2', shown in dashed and dotted lines in FIG. 3, this container being able to be a supple bag containing a liquid intended to dissolve or place in suspension the product contained in the recipient 2, for example the active ingredient of a medicament.

The recipient 2 comprises a neck 3 whose opening 3*a* is hermetically stopped by a stopper 4, made of a relatively non-rigid material, for example elastomer and in particular rubber. The neck 3 comprises an outer annular bead 3*b* serving for assembly and fixation of a base 5.

The stopper 4 comprises a cylindrical central part 4*a*, adapted for a supple and tight fit inside the opening 3*a* of the neck 3, and a flattened outer part 4*b* shouldered on the bead 3*b*.

The base 5 is made in one piece of a plastics material which is relatively hard with respect to the material constituting the stopper 4. It comprises a plurality of hooking teeth 6 provided to be disposed around the bead 3*b* of the neck 3, in the manner shown in FIG. 2 and in accordance with the technical teaching of WO-A-97/10156.

The base 5 comprises a wall 8 bearing on the part 4*b* of the stopper 4, this wall being provided with a central recess 8*a* whose function will be explained hereinafter. The wall 8 also bears two circular ribs 8*b* and 8*c* oriented towards the stopper 4 and provided to penetrate in the outer part 4*b* of the stopper 4, with the result that they create a tight barrier between the wall 8 and the stopper 4. The base 5 extends in a flange 9, oriented opposite the teeth 6 with respect to the wall 8 and of which the inner radial surface 9*a* defines a bore A of substantially circular section.

A plunger 10 is provided to slide inside the bore A in a direction defined by the axis of symmetry X–X' of this bore, which axis is also the axis of symmetry of the base 5 around which the teeth 6 are distributed.

The plunger 10 comprises a section 10*a* substantially perpendicular to the axis X–X' and a skirt 10*b* in the form of a cylindrical sleeve centred on axis X–X'. A hollow needle 11 borne by the section 10*a* of the plunger 10 is centred on axis X–X'. The skirt 10*b* of the plunger 10 bears a shoulder 10*c* while the flange 9 is provided with a peripheral inner projection 9*b* at the level of the opening of the bore A. As is more clearly visible in FIG. 2, the plunger 10 may be introduced inside the bore A, by elastic deformation of the flange 9, in a position such that the shoulder 10*c* is in contact with the projection 9*b*, the plunger 10 in that case being locked inside the bore A. In this position, the needle 11 is disengaged with respect to the stopper 4, i.e. does not perforate this stopper.

Figure 2:
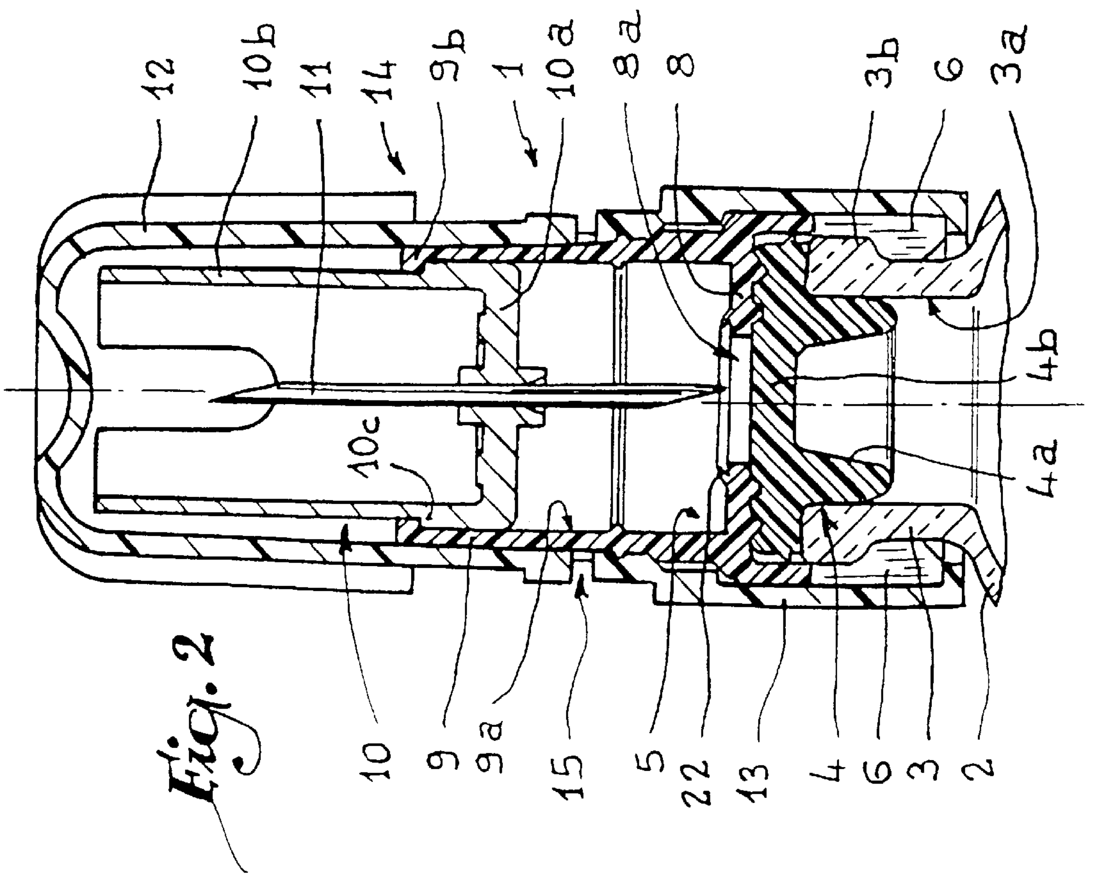
FIG. 2 is a longitudinal section of the device of FIG. 1 mounted on the recipient, the whole being in a configuration of storage.

A cap 12 is provided to be disposed around the assembly formed by the base 5 and the plunger 10 and comprises a lower ring 13, adapted to lock the teeth 6 of the base 5 around the neck 3, and a breakable part 14 intended to protect the plunger 10 in the position of FIG. 2, this breakable part being connected to the ring 13 by a line of break 15.

Figure 3:
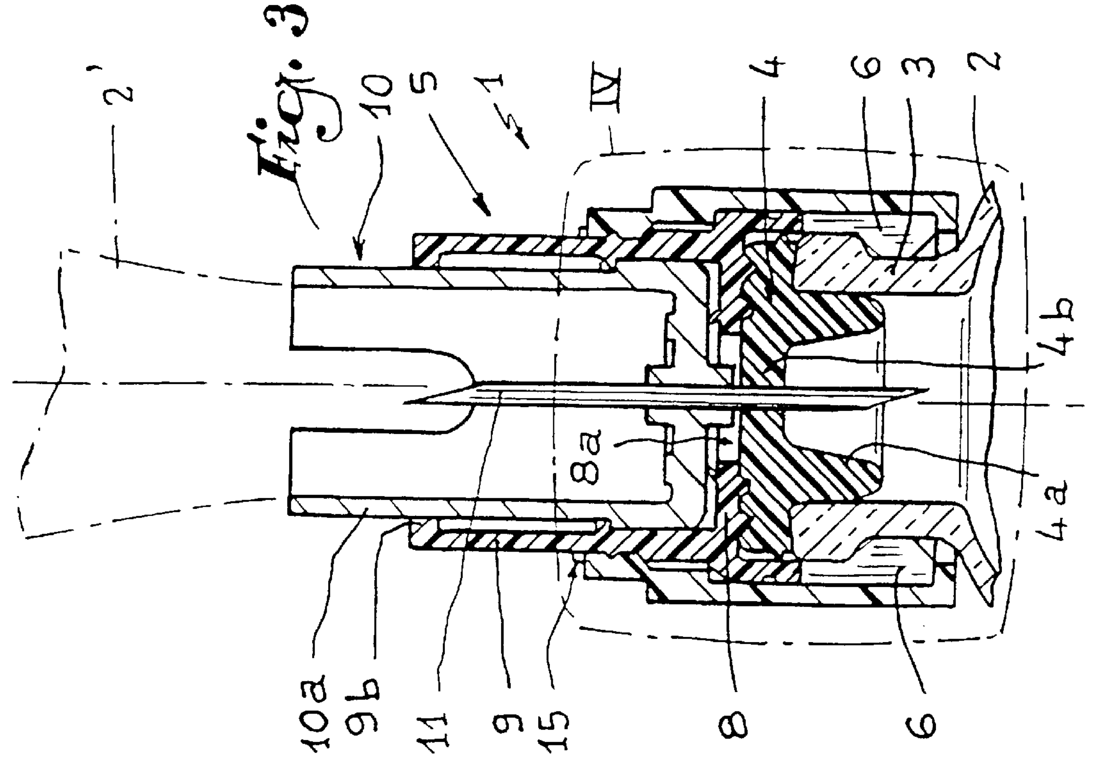
FIG. 3 is a longitudinal section similar to FIG. 2 while the plunger of the device has been displaced towards a transfer position between the inner volume of the recipient and the outside.

When it is necessary to use the product contained in the recipient 2, it suffices to separate the breakable part 14 from the rest of the cap 12 in order to have access to the plunger 10 which may in that case be pushed in the direction of the recipient 2 in order to reach the transfer position shown in FIG. 3 in which the needle 11 has traversed the recess 8*a* of the wall 8 and perforated the stopper 4.

In order that a user can effectively displace the plunger 10 in the direction of the stopper 4, the radial clearance J between the surface 9*a* and the skirt 10*b* must not be too small, otherwise the device would risk being blocked. It is therefore not excluded that the orifice 20, formed by the needle 11 in the stopper 4 and which is of cylindrical shape, has an axis slightly inclined with respect to axis X–X', which has been represented, in exaggerated manner, with axis Y–Y' in FIG. 4.

According to the invention, the face 8*d* of the wall 8 oriented towards the plunger 10 bears a lip 22 directed towards the front face 10*d* of the section 10*a* of the plunger 10. The lip 22 is in one piece with the wall 8, itself in one piece with the rest of the base 5 which is made of plastics material harder than the stopper 4, but presenting a suppleness allowing deformation of the lip 22.

Figure 4:
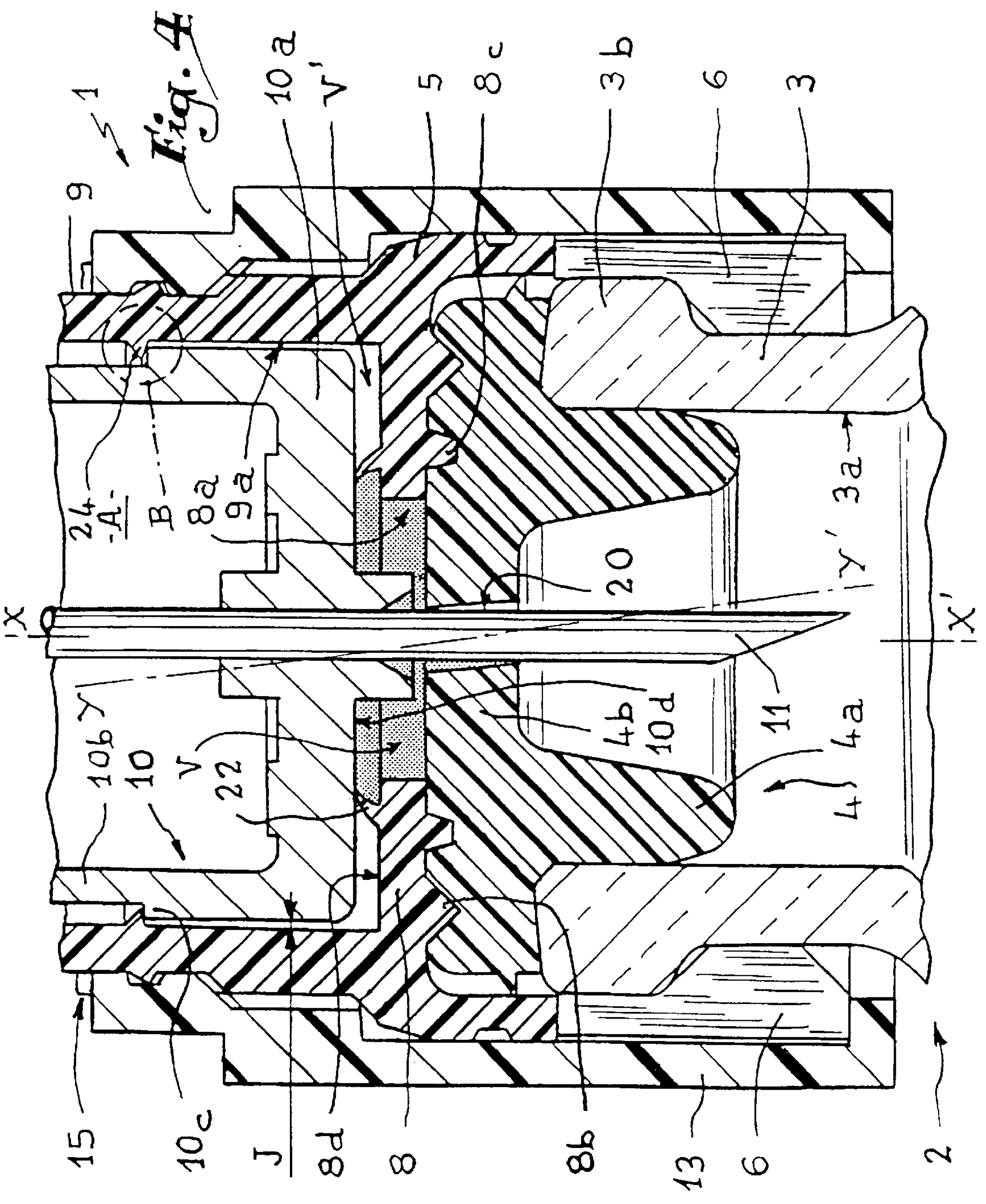
FIG. 4 is a view on a larger scale of detail IV of FIG. 3.

The lip 22 is circular, i.e. extends over a circumference centred on axis X–X', with the result that, when it is in contact with the front face 10*d* of the plunger 10, it closes a volume V for containment of a possible leakage of liquid through the orifice 20, this volume being represented in grey tint in FIG. 4.

Figure 4B:
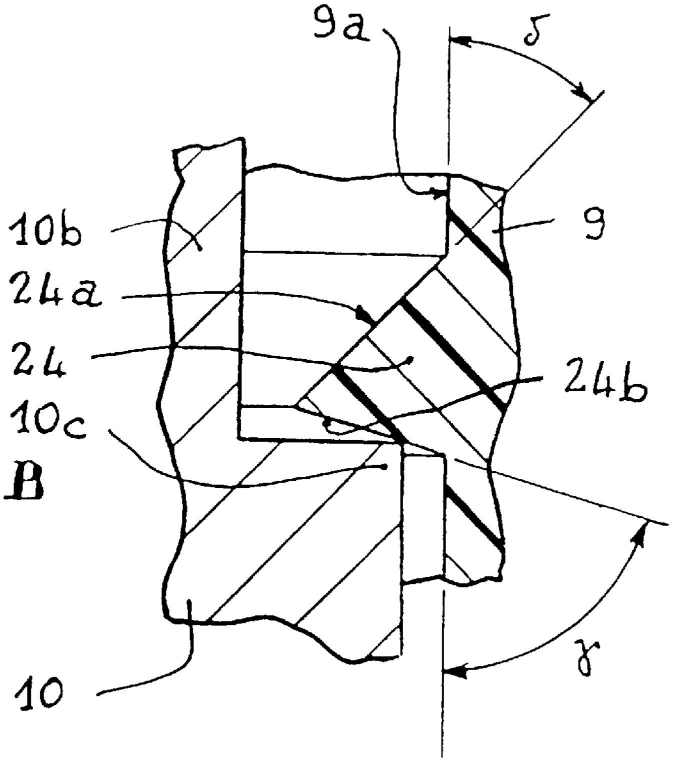
FIG. 4B is a view on a larger scale of detail B of FIG. 4.
Figure 4A:
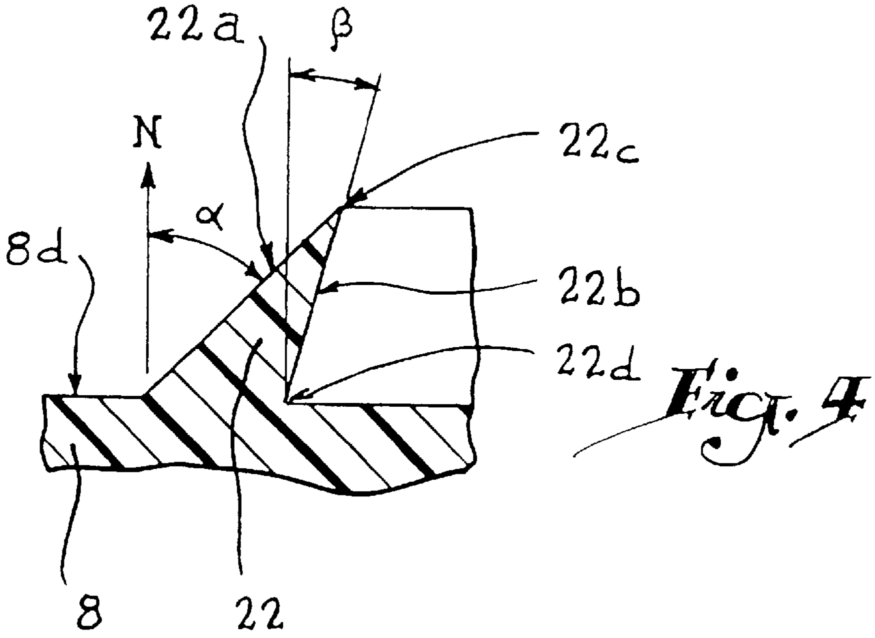
FIG. 4A is a section on a larger scale of the sealing lip of the device at rest, i.e. in the position of FIG. 2.

At rest and as shown in FIG. 4A, the lip 22 has an asymmetrical cross section in the form of an inclined tooth. The angle of inclination $\alpha$ of its outer face 22*a* with respect to a normal N to the face 8*d* is greater than the angle $\beta$ of its inner face 22*b* with respect to a normal N' to the face 8*d*. The edge 22*c* of the lip 22 projects inwardly with respect to the foot 22*d* of the inner face 22*b*. In this way, the direction of crushing of the lip 22 upon abutment of the front face 10*d* is turned towards axis X–X' so that the tightness is effected with the outer face 22*a* of the lip 22 having a tangent substantially parallel to the front face 10*d* of the plunger 10, which guarantees an optimal seal, including when the pressure of the plunger 10 on the lip 22 is not very high.

The lip 22 exerts on the plunger 10 an effort of reaction which increases when liquid is present in the volume V, this liquid exerting a pressure on the inner face 22*b* of the lip 22, which pressure tends to return the lip 22 into its configuration of FIG. 4A.

A ring 24 is provided on the inner radial surface 9*a* of the flange 9, at such a height with respect to the wall 8 that it cooperates with the shoulder 10*c* of the skirt 10*b* to block the plunger 10 in the transfer position of FIGS. 3 and 4. The ring 24 advantageously extends over the whole circumference of the surface 9*a* and presents, in transverse section and as shown in FIG. 4B, a face 24*a* directed towards the opening of the bore A and a face 24*b* directed towards the bottom of this bore, i.e. towards the stopper 4 and the wall 8. The angle of inclination $\delta$ of the surface 24*a* with respect to the surface 9*a* is of the order of 30°, while the angle of inclination $\gamma$ of the surface 24*b* with respect to this same surface is of the order of 60'. This asymmetrical shape of the ring 24 allows it not to oppose the movement of drive of the plunger 10 inside the bore A too strongly, as the face 24*a* is hardly inclined with respect to axis X–X', while it efficiently locks the shoulder 10*c* thanks to the considerable inclination of its face 24*b*.

The function of locking of the ring 24 makes it possible to guarantee that an adequate pressure is exerted by the plunger 10 on the lip 22 in order to obtain a satisfactory seal.

As the ring 24 extends over the whole periphery of the surface 9*a*, it also contributes to the seal of the whole of the device 1 insofar as liquid, which might reach to outside the volume V due to a leakage at the level of lip 22, would remain contained in the volume V' defined between the front face 10*d* and the wall 8 outside the lip 22 and by the annular clearance J between the skirt 10*b* and the surface 9*a*, at the level of the front of the plunger 10. The ring 24 therefore has a dual function of locking and of sealing.

Figure 5:
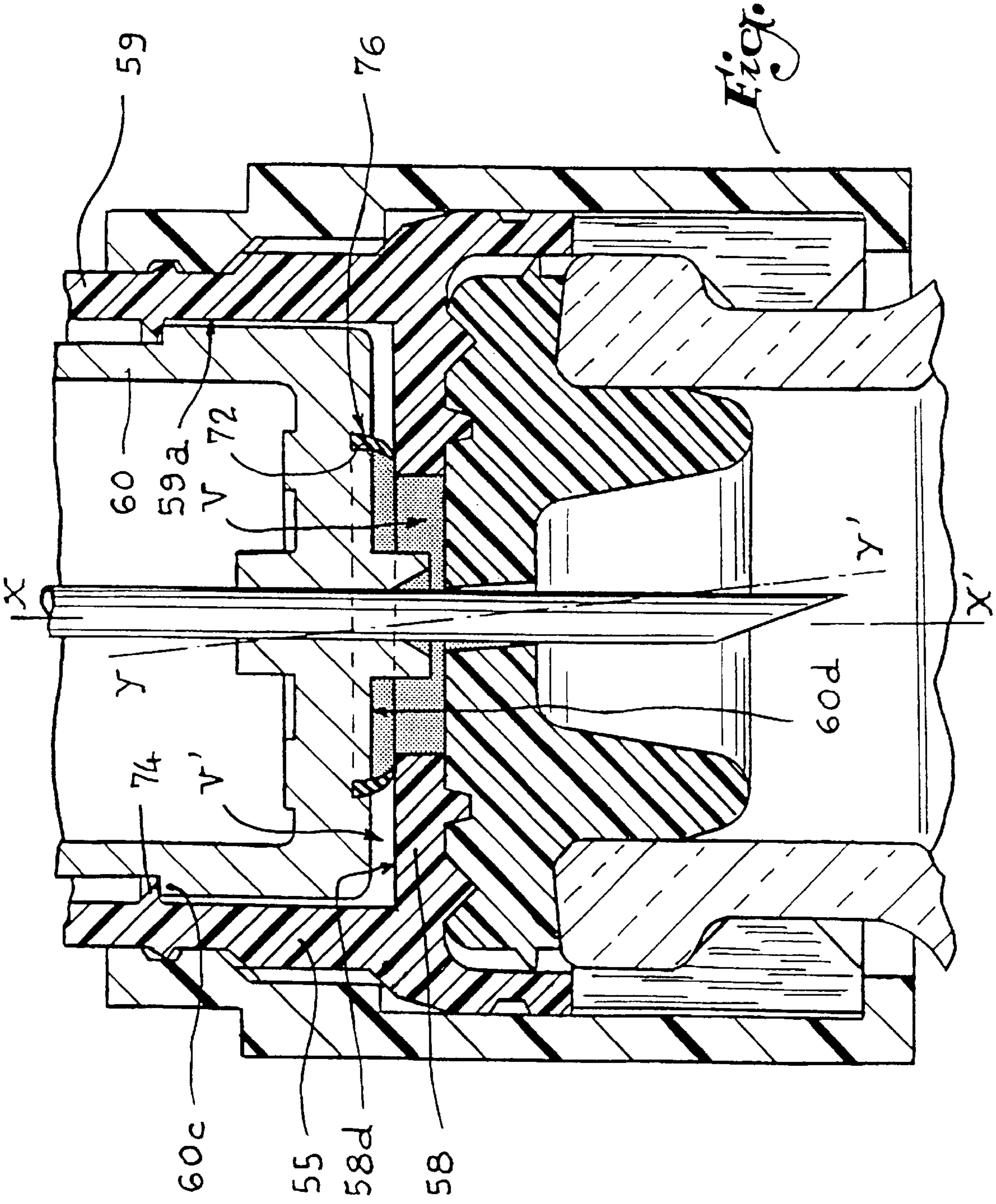
FIG. 5 is a view similar to FIG. 4 for a device in accordance with a second embodiment of the invention.

In the second embodiment of the invention shown in FIG. 5, elements similar to those of the embodiment of FIGS. 1 to 4 bear identical references increased by 50. The device of this embodiment differs from the preceding one essentially in that the sealing lip 72 is borne by the front face 60*d* of the plunger 60 and provided to come into contact with the upper face 58*d* of the partition 58 of the base 55. The lip 72 therefore makes it possible to define a volume V for containment of a possible leakage of liquid. A ring 74 is also provided on the inner radial surface 59*a* of the flange 59 for locking the plunger 60 in position with respect to the base 55 and in order to constitute a second sealing barrier for a second closed volume V'. The plunger 60 bears a shoulder 60*c* adapted to cooperate with the ring 74. The front face 60*d* of the plunger 60 bears a groove 76 inside which is immobilized the lip 72 which may be made of a material distinct from that of the plunger 72 and, in particular, of a more supple material allowing an increased deformation during abutment of the plunger 60 against the wall 58, in order to improve seal.

The lip 72 is immobilized in the groove 76 by any appropriate means and, in particular, by cooperation of shapes and/or adhesion.

Figure 6:
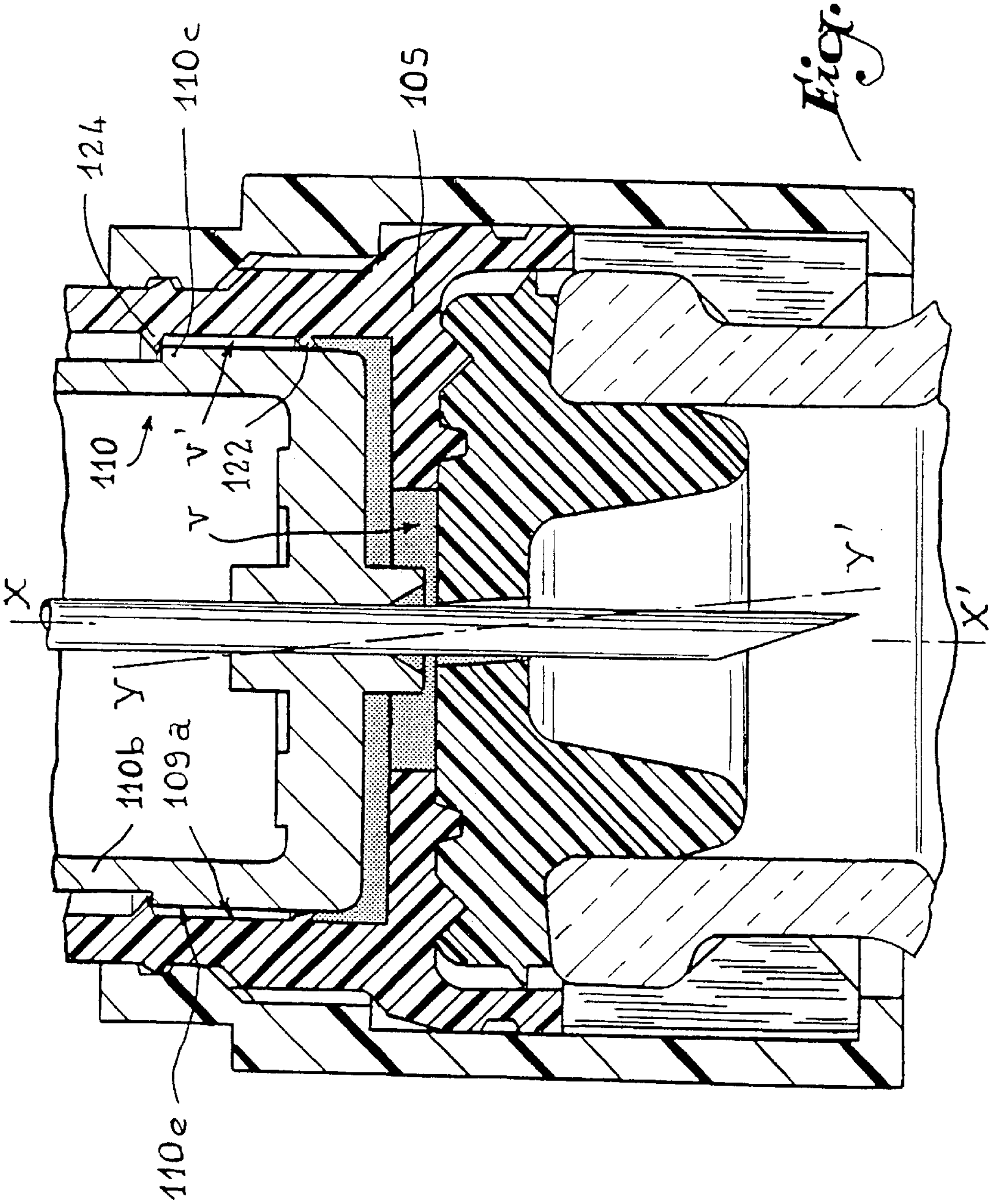
FIG. 6 is a view similar to FIG. 4 for a device in accordance with a third embodiment of the invention.

In the third embodiment of the invention shown in FIG. 6, elements similar to those of the embodiment of FIGS. 1 to 4 bear identical references increased by 100. A sealing lip 122 is provided on the inner radial surface 109*a* of the flange 109 opposite the outer radial surface 110*e* of the skirt 110*b* of the plunger 110 to define a volume of containment V. As before, a ring 124 is provided on the surface 109*a* for immobilizing a shoulder 110*c* of the plunger 110 with respect to the base 105 in the transfer position. It also performs the role of sealing barrier for a second closed volume V'.

According to a variant of the invention (not shown) and taking a mirror solution with respect to that of the embodiment of FIG. 6, the sealing lip might be borne by the outer surface 110*e* of the skirt 110. Similarly, the skirts 22 and 122 might be constituted by elements added on the base, in accordance with a technique similar to that evoked with reference to the embodiment of FIG. 5. Of course, the lip borne by the plunger in the embodiment of FIG. 5 might also be in one piece with this plunger.

It will be noted that the lips 72 and 122 have an asymmetrical profile, like lip 22, which gives them a privileged direction of deformation.

It is possible to provide for the ring 24, 74 or 124 to be formed by discrete, i.e. non-contiguous angular sectors, in which case it efficiently performs its function of locking but does not participate in the seal of the volume V'.

Whatever the embodiment considered, the immobilization of the plunger 10, 60 or 110 thanks to ring 24, 74 or 124 guarantees a constant positioning of the needle 11 or equivalent, with respect to the recipient 2, with the result that the lost volume of the recipient 2, i.e. the quantity of product contained in the recipient which cannot be recovered due to the distance between the end of the needle 11 and the neck of the recipient, is constant from one device to another. The quantity of product introduced in the recipient 2 or equivalent before its obturation by the corresponding stopper can therefore be determined with precision, taking into account this constant lost volume.

It will be noted that the invention is applicable independently of the mode of fixing the base 5 on the recipient 2 and, generally, that it may be used in any connection device comprising a plunger, mobile inside a bore of a base mounted on a recipient.

What is claimed is:

1. Device for connection between a closed recipient and a container, said recipient comprising a neck with an opening obturated by a stopper, said device comprising: a base, mounted on said recipient and extending in a flange forming an inner bore, a plunger adapted to slide in said inner bore, between a position disengaged with respect to said stopper and a transfer position in which a hollow needle borne by said plunger traverses said stopper; and a sealing lip provided on an internal surface of said inner bore opposite said plunger or on a surface of said plunger, said sealing lip being shaped to be in tight abutment against said plunger or against an internal surface of said inner bore, in said transfer position of said plunger.

2. Device according to claim 1, wherein said inner base comprises a wall for abutment against an outer part of said stopper, said sealing lip on a face of said wall oriented towards said plunger.

3. Device according to claim 1, wherein said sealing lip is shaped on a front face of said plunger oriented towards said stopper.

4. Device according to claim 1, wherein said sealing lip is shaped on an inner radial surface of said flange or on an outer radial surface of said plunger.

5. Device according to claim 4, wherein said sealing lip presents, in cross-section, an asymmetrical profile inducing a privileged direction of deformation.

6. Device according to claim 1, wherein said flange bears, on an inner radial face, a circular ring adapted to cooperate with a corresponding shoulder of an outer radial surface of said plunger in order to lock said plunger in said transfer position.

7. Device according to claim 6, wherein said circular ring is disposed so that it locks said plunger in a position of tight bearing said sealing lip against said plunger or against an inner portion of said inner bore.

8. Device according to claim 6, wherein said circular ring presents an asymmetrical cross-section, the face of said circular ring oriented towards the opening of said inner bore being less inclined with respect to the inner radial surface of said flange than the face of said circular ring oriented towards said stopper.

9. Device according to claim 6, wherein said circular ring is adapted to separate an annular volume, defined in said inner bore around a front part of said plunger in transfer position, hermetically with respect to the ambient temperature.

10. Ready-for-use assembly, comprising a closed recipient containing a product, said recipient comprising a neck whose opening is obturated by a stopper and a connection device mounted on said recipient; said connection device further comprising: a base, mounted on said closed recipient between said closed recipient and a container and extending in a flange forming an inner bore, a plunger adapted to slide in an inner bore, between a position disengaged with respect to said stopper and a transfer position in which a hollow needle borne by said plunger traverses said stopper, and; a sealing lip provided on an internal surface of said inner bore opposite said plunger or on a surface of said plunger, said sealing lip being shaped to be in tight abutment against said plunger or against and internal surface of said bore, in said transfer position of said plunger.

11. Device for connection between a closed recipient and a container, said recipient comprising a neck with an opening obturated by a stopper, said device comprising:

a base adapted to be mounted on said recipient and extending in a flange forming an inner bore;

a plunger slideable in said inner bore, between a position disengaged with respect to said stopper and a transfer position in which a hollow needle borne by said plunger traverses said stopper;

a sealing lip provided on an internal surface of said inner bore opposite said plunger or on a surface of said plunger, said sealing lip being shaped to be in tight abutment against said plunger or against and internal surface of said bore, in said transfer position of said plunger said flange bears, on an inner radial face; and, a circular ring bearing from an inner radial face of said flange to cooperate with a corresponding shoulder of an outer radial surface of said plunger in order to lock said plunger in said transfer position, wherein said ring separates an annular volume, defined in said inner bore around a front part of said plunger in the transfer position, hermetically with respect to the ambient atmosphere.

12. A device for connection between a closed recipient and a container, said recipient having a neck with an opening obturated by a stopper, said device comprising:

a base adapted to be mounted on said recipient, the base having a flange forming an inner bore;

a plunger having a needle, the plunger slidable in said inner bore between a position disengaged with respect to said stopper and a transfer position wherein the needle is adapted to traverse said stopper; and a sealing lip located on one of the base and the plunger and an abutment surface located on the other of the base and the plunger, wherein the sealing lip is shaped to be in tight abutment against the abutment surface when the plunger is in the transfer position.

13. The device according to claim 12 wherein said sealing lip is located on said plunger and said abutment surface is located on said base.

14. The device according to claim 12 wherein said sealing lip is located on said base and said abutment surface is located on said plunger.

15. The device according to claim 14 wherein said sealing lip is located on an inner radial surface of the flange and said abutment surface is located on an outer radial surface of the plunger.

16. The device according to claim 14 wherein the said sealing lip is located on a front face of a wall directed towards a face of said plunger and said abutment surface is located on the face of said plunger.

* * * * *

UNITED STATES PATENT AND TRADEMARK OFFICE

CERTIFICATE OF CORRECTION

PATENT NO. : 6,537,263 B1
DATED : March 25, 2003
INVENTOR(S) : Antoine Aneas

It is certified that error appears in the above-identified patent and that said Letters Patent is hereby corrected as shown below:

Column 1,
Line 18, "WO-A-97110156" should read -- WO-A-97/10 156 --.

Signed and Sealed this

Twenty-eighth Day of October, 2003

JAMES E. ROGAN
*Director of the United States Patent and Trademark Office*